US012661266B2

(12) United States Patent
Ravilla Kasthuri et al.

(10) Patent No.: US 12,661,266 B2
(45) Date of Patent: Jun. 23, 2026

(54) SINGLE AND/OR DUAL (532 AND/OR 577) NM LASER DELIVERY SYSTEM ATTACHED TO AN OPHTHALMIC MICROSCOPE

(71) Applicant: APPASAMY ASSOCIATES PVT LTD, Chennai (IN)

(72) Inventors: Narayanasamy Ravilla Kasthuri, Chennai (IN); Sri Rama Prasad Jeyaraj, Chennai (IN)

(73) Assignee: APPASAMY ASSOCIATES PVT LTD, Chennai (IN)

( * ) Notice: Subject to any disclaimer, the term of this patent is extended or adjusted under 35 U.S.C. 154(b) by 234 days.

(21) Appl. No.: 18/294,321

(22) PCT Filed: Oct. 13, 2022

(86) PCT No.: PCT/IN2022/050912
§ 371 (c)(1),
(2) Date: Feb. 1, 2024

(87) PCT Pub. No.: WO2023/062650
PCT Pub. Date: Apr. 20, 2023

(65) Prior Publication Data
US 2024/0335324 A1     Oct. 10, 2024

(30) Foreign Application Priority Data

Oct. 14, 2021    (IN) ............................. 202141031550

(51) Int. Cl.
*A61F 9/008*        (2006.01)
*A61B 18/00*        (2006.01)
(Continued)

(52) U.S. Cl.
CPC ............ *A61F 9/0084* (2013.01); *A61B 90/20* (2016.02); *A61F 9/00834* (2013.01);
(Continued)

(58) Field of Classification Search
None
See application file for complete search history.

(56) References Cited

U.S. PATENT DOCUMENTS

| | | | |
|---|---|---|---|
| 5,426,662 A | 6/1995 | Mefferd et al. | |
| 5,954,711 A | 9/1999 | Ozaki et al. | |

(Continued)

FOREIGN PATENT DOCUMENTS

| | | |
|---|---|---|
| KR | 101177478 B1 | 8/2012 |
| KR | 102190881 B1 | 12/2020 |

(Continued)

OTHER PUBLICATIONS

International Search Report & Written Opinion dated Feb. 2, 2023 from PCT Application No. PCT/IN2022/050912, 8 pages.

*Primary Examiner* — Michael W Kahelin
(74) *Attorney, Agent, or Firm* — INNOVATION CAPITAL LAW GROUP, LLP; Vic Lin

(57) ABSTRACT

The present invention relates to a single and/or dual laser delivery system attached to an existing ophthalmic operating microscope, comprising of a single and/or dual wavelength laser unit [1]; and a delivery system [5]. The laser unit [1] comprises of a green laser module 532 nm [3] and a yellow laser module 577 nm [4] along with an aiming beam [7] 635 nm. The delivery system comprises of a right-angle prism [5A]: X and Y Galvo assembly [5B] and a focusing lens assembly [5C]. The laser unit passes through a fiber optic cable [6] gets reflected using the right angle prism, gets deflected by the Galvo assembly, enters the focusing lens assembly and gets reflected by a folding mirror [5D] and focused on human eye capsule. The system converges and focuses the laser wavelengths in line with the aiming beam to create a circular pattern to accomplish a pre-measured Capsulorhexis.

6 Claims, 5 Drawing Sheets

(51) Int. Cl.
    *A61B 18/20*       (2006.01)
    *A61B 90/20*       (2016.01)

(52) U.S. Cl.
    CPC ............... *A61B 2018/00601* (2013.01); *A61B 2018/2025* (2013.01); *A61B 2018/20355* (2017.05); *A61B 2018/20553* (2017.05); *A61B 2018/207* (2013.01); *A61F 2009/0087* (2013.01)

(56) References Cited

U.S. PATENT DOCUMENTS

| | | | |
|---|---|---|---|
| 8,315,280 B2 | 11/2012 | Zimare et al. | |
| 9,895,056 B2 | 2/2018 | Klaffenbach et al. | |
| 10,022,270 B2 | 7/2018 | Schuele et al. | |
| 10,433,718 B2 | 10/2019 | Liolios et al. | |
| 10,596,037 B2 | 3/2020 | Tedford et al. | |
| 11,083,625 B2 | 8/2021 | Schuele et al. | |
| 2011/0202046 A1* | 8/2011 | Angeley | A61F 9/009 606/6 |
| 2013/0072917 A1 | 3/2013 | Kaschke et al. | |
| 2014/0107634 A1 | 4/2014 | Vogler et al. | |
| 2024/0197533 A1* | 6/2024 | Dolzan | A61F 9/00821 |

FOREIGN PATENT DOCUMENTS

| | | | |
|---|---|---|---|
| WO | 9301638 A1 | 1/1993 | |
| WO | 2015131135 A1 | 9/2015 | |

\* cited by examiner

To Human Eye          From Fiber Optic Cable 5.5 mm 5.5 mm with Measurement 5 mm 5 mm with measurement

A

B

C

D

SINGLE AND/OR DUAL (532 AND/OR 577) NM LASER DELIVERY SYSTEM ATTACHED TO AN OPHTHALMIC MICROSCOPE

FIELD OF INVENTION

The present invention relates to a laser unit, particularly to single and/or dual (532 and/or 577) nm laser delivery system attached to an existing ophthalmic operating microscope for creation of a Capsulorhexis in a human eye.

BACKGROUND OF INVENTION

Capsulorhexis generally refer to removal of a part of the capsule by shear and stretch forces, but in situations like a developmental cataract a part of the capsule is also removed by a similar technique. A cataract is a dense, cloudy area that forms in the lens of an eye. Creation of the Capsulorhexis is a key stage in cataract surgery, and producing a precise rhexis is of paramount importance. Capsulorhexis was first performed by removing the lens and safely implanting intraocular lens (IOL) in the capsular bag. This procedure avoided the radial tears which occurred frequently in the can-opener capsulotomies that were performed at the time. A correctly sized, and a well-centered Capsulorhexis with a 360° overlapping capsular edge prevents IOL tilt, myopic shift, optic de-centration, and posterior and anterior capsular opacification, partly due to a combination of the symmetric contractile forces of the capsular bag, and the shrink wrap effect. However, eccentric or irregularly shaped Capsulorhexis with a diameter extending beyond the optic edge may lose these advantages.

Currently, Capsulorherxis step is being done during Phacosurgery either by manually using a 26G needle or forceps. The selection depends on the length of the incision that the surgeon chooses to make. However, the manual procedure is time consuming and also involves surgeon's skill. Also, in manual procedure, it is essential that capsule tear direction is controlled, as the overall direction of pulling forces on the capsule flap can cause different tearing direction patterns. Recently Capsulorherxis step is being done using a Femtosecond laser which is a newer technology and very expensive investment too for individual practitioners. Further, it also requires a separate specialized operation room with accurately maintained room temperature for its perfect functioning hence very high recurring maintenance cost. However, in the Femtosecond laser assisted cataract surgery, the laser equipment and the ultrasonic emulsification equipment are not integrated, the operation process needs to be carried out separately in two different operation rooms, which also involves shifting of the patient from one operating room to an another operating room and hence the operation time is prolonged. In addition, patients with primary diseases of small pupils and corneal epithelium and adverse eye socket shapes to the connection of laser equipment and eyes are not suitable for Femtosecond laser-assisted cataract surgery.

U.S. Ser. No. 11/083,625B2 discloses a system for laser ophthalmic surgery comprising of laser assembly, confocal detection assembly and scanning assembly. The system has used two treatment lasers.

First treatment laser is infrared wavelength 870 nm to 1200 nm and second treatment laser is ultraviolet wavelength 320 nm to 370 nm. The focal spot size is 150 microns.

U.S. Pat. No. 9,895,056B2 discloses an ophthalmic laser illuminator with three different wavelength lasers Red (At least 620 nm), Blue (less than 480 nm), Green (between 552 nm and 557 nm). The illuminator has mixer/homogenizer for mixing the three wavelengths of light.

U.S. Pat. No. 8,315,280B2 relates to multiple wavelength laser system which includes at least two semiconductor diode lasers and one light guide system. The wavelength ranges are 480 nm to 520 nm, 530 to 550 nm, 560 to 580 nm and 1040 nm to 1070 nm. However, the purpose is for therapeutic sectors that include photocoagulation, transpupillary thermotherapy, photothermal tumor treatment and photodynamic therapy.

U.S. Pat. No. 5,426,662A discloses a laser system for ophthalmological treatments with two competing wavelength regions. The wavelength regions are reflective at 647 nm and transmissive at 531 nm and 568 nm.

U.S. Ser. No. 10/022,270B2 discloses methods and systems for performing laser-assisted surgery. The wavelength range is from 500 nm to 1100 nm and the focal spot has a diameter of 1 to 20 microns.

U.S. Ser. No. 10/596,037B2 relates to an ophthalmic phototherapy device which promotes the healing of damaged or diseased eye tissue. The system uses multiple wavelengths and the ranges are 500 nm to 650 nm or 640 nm to 700 nm or 800 nm to 900 nm.

WO2015131135A1 discloses laser assisted cataract surgery methods and devices which utilize one or more treatment laser beams to create a shaped opening in the anterior lens capsule of the eye when performing a capsulorrhexis procedure. The laser may operate at a wavelength of about 577 nm or about 590 nm or about 810 nm. The spot size of laser is 100 microns to 350 microns.

KR102190881B1 discloses a laser device for high-intensity pain treatment using a composite wavelength and a programmed scan handpiece. The wavelength band of the laser beam is any one of 980 nm and 1064 nm in the case of a short wavelength, and provides a combined wavelength of 980 nm and 1064 nm in the case of a complex wavelength.

WO1993001638A1 discloses a laser system with dielectric mirror, laser medium and motor driven carriage. The laser medium utilizing a YAG type crystal to make it possible, the generation of wavelengths of 1064 nm, 1320 nm, 532 nm and 660 nm from a single laser system.

KR101177478B1 discloses a laser apparatus with laser oscillating unit, power converting unit, an optical coupling unit, laser output cut-off unit and a scope unit to controls the direction or spot size of a laser beam. The laser apparatus use dual wavelength namely yellow wavelength (578 nm) and green wavelength (511 nm).

Accordingly, there exists a need for a compact, precision, safety and cost effective single and/or dual wavelength laser unit with a delivery system that could be retrofitted to an existing ophthalmic operating microscope to overcome the afore-mentioned drawbacks.

OBJECTS OF INVENTION

One or more of the problems of the conventional prior art may be overcome by various embodiments of the system and method of the present invention.

It is the primary object of the present invention to provide a compact, cost effective single and/or dual wavelength laser unit with a delivery system attached to an existing ophthalmic operating microscope.

It is another object of the present invention to provide a single and/or dual wavelength laser delivery system attached to an existing ophthalmic operating microscope to create a circular pattern to accomplish a pre-measured diameter size of Capsulorhexis with a precise circular cut of the capsule in human eye with a precise diameter of 3 mm to 6 mm in steps of 0.5 mm.

It is another object of the present invention to provide a Galvo assembly driven single and/or dual wavelength laser delivery system attached to an existing ophthalmic operating microscope for laser beam to be focused on to the capsular bag in the human eye.

It is another object of the present invention, wherein the laser delivery system converges and focuses the single and/or dual wavelength laser beam to create a circular pattern in order to accomplish a pre-measured Capsulorhexis with a precise circular cut of the capsule in the human eye with a precise diameter of 3 mm to 6 mm in steps of 0.5 mm.

It is another object of the present invention, wherein the laser delivery system has an aiming beam which is used to locate and guide user to aim the single and/or dual wavelength laser beam before the Capsulorhexis.

SUMMARY OF INVENTION

Thus according to the basic aspect of the present invention, there is provided a single and/or dual wavelength laser delivery system attached to an existing ophthalmic operating microscope, said system comprises of:

a single and/or dual wavelength laser unit;

a delivery system; and an ophthalmic operating microscope, wherein the single and/or dual wavelength laser unit comprises of a green laser module 532 nm and a yellow laser module 577 nm along with an aiming beam 635 nm within both the laser modules to create a circular pattern with a precise circular cut of the capsule in a human eye, wherein the aiming beam 635 nm is used to locate and guide user to aim the 535 nm and/or 577 nm laser beam, wherein each of the laser modules comprises of a low pass filter and a focusing lens respectively, wherein the green and yellow laser modules are connected to the delivery system through an interchangeable single fiber optic cable, wherein the delivery system comprises of a right-angle prism; a X and Y Galvo assembly and a focusing lens assembly, wherein the single and/or dual wavelength module from the laser unit passes through the fiber optic cable gets reflected using the right angle prism, gets deflected by the X and Y Galvo assembly, enters the focusing lens assembly and gets reflected by a folding mirror and focused on the human eye capsule at 90 degrees, and wherein said laser delivery system attached to the operating microscope's converges and focuses the laser wavelength of 532 nm and/or 577 nm laser beam in-line with the 635 nm aiming beam to create a circular pattern to accomplish a pre-measured Capsulorhexis with a precise circular cut of the capsule in the human eye.

It is another aspect of the present invention, wherein the low pass filters are mounted at an angle that transmits the 532 nm green laser or 577 nm yellow laser beam and reflects the 635 nm aiming beam.

It is another aspect of the present invention, wherein the laser beam from the fiber optic cable passes through the focusing lens assembly to get a required spot size of 100 microns to 300 microns.

It is another aspect of the present invention, wherein the folding mirror is mounted in an angle of 45 degree with a tolerance level of + or −2 degrees along the laser optical axis.

It is another aspect of the present invention, wherein the single and/or dual wavelength laser delivery system converges and focuses the laser wavelength of 532 nm and/or 577 nm laser beam in-line with the 635 nm aiming beam to create a circular pattern to accomplish a pre-measured Capsulorhexis with a precise circular cut of the capsule in the human eye with a precise diameter of 3 mm to 6 mm in steps of 0.5 mm.

It is another aspect of the present invention, wherein the laser unit comprises a foot switch to trigger the 532 nm and/or 577 nm laser beam.

DETAILED DESCRIPTION OF THE INVENTION WITH REFERENCE TO THE ACCOMPANYING FIGURES

The present invention as herein described relates to a single and/or dual (532 and/or 577) nm laser delivery system attached to an existing ophthalmic operating microscope for creation of circular pattern to accomplish a pre-measured diameter size of capsulorhexis.

Figure 1:
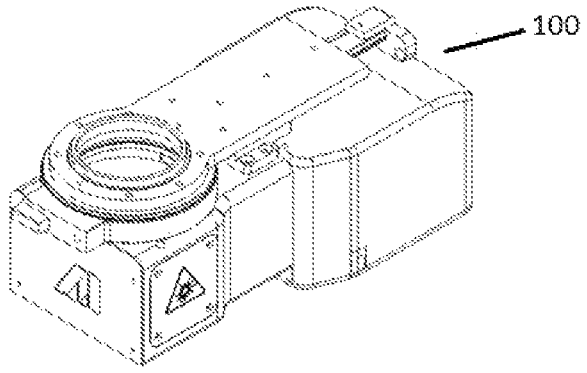
FIG. 1: illustrates single and/or dual wavelength laser delivery system according to the present invention.
Figure 2:
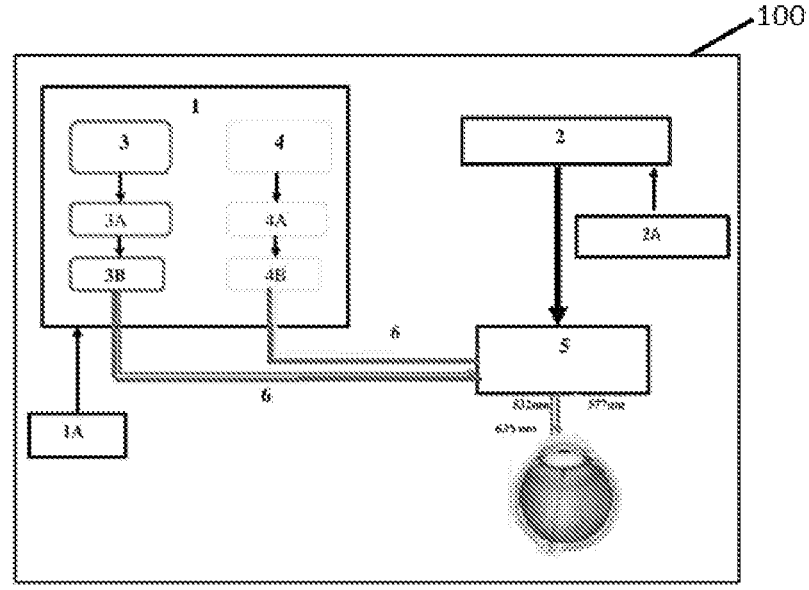
FIG. 2: illustrates block diagram of single and/or dual wavelength laser delivery system according to the present invention.
Figure 3:
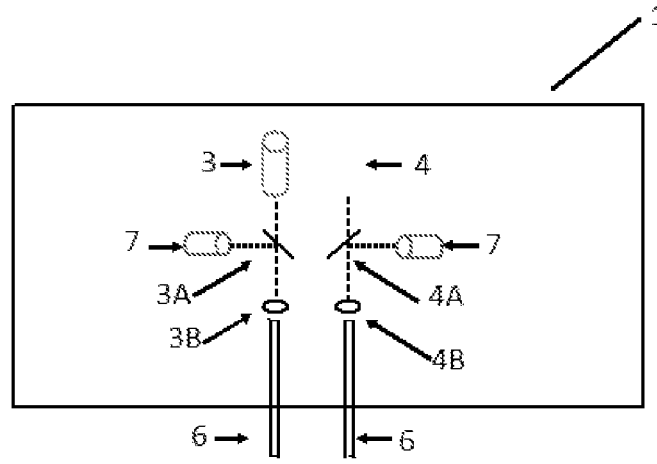
FIG. 3: illustrates laser unit of the system according to the present invention.

Referring to FIGS. 1 to 3, the single and/or dual wavelength laser delivery system [100] comprises of a single and/or dual wavelength laser unit [1]; a delivery system [5]; and an ophthalmic operating microscope [2]. The laser unit [1] comprises of a green laser module 532 nm [3] and a yellow laser module 577 nm [4] along with 635 nm aiming beam [7] (as shown in FIG. 3) within both the laser modules [3 and 4] to create a circular pattern with a precise circular cut of the capsule in the human eye. The 635 nm aiming beam [7] is used to locate and guide the user to aim the 535 nm and/or 577 nm laser beam on the human eye capsule before the Capsulorhexis. The green laser module [3] comprises of a low pass filter [3A] and a focusing lens [3B]. The yellow laser module [4] comprises of a low pass filter [4A] and a focusing lens [4B]. The low pass filters [3A and 4A] are mounted at an angle that transmits the 532 nm green laser [3] or 577 nm yellow laser beam [4] and reflects the 635 nm aiming beam [7]. The laser modules [3 and 4] are connected to the delivery system [5] through an interchangeable single fiber optic cable [6]. The laser unit [1] includes a foot switch [1A] to trigger the laser beam.

Figure 4:
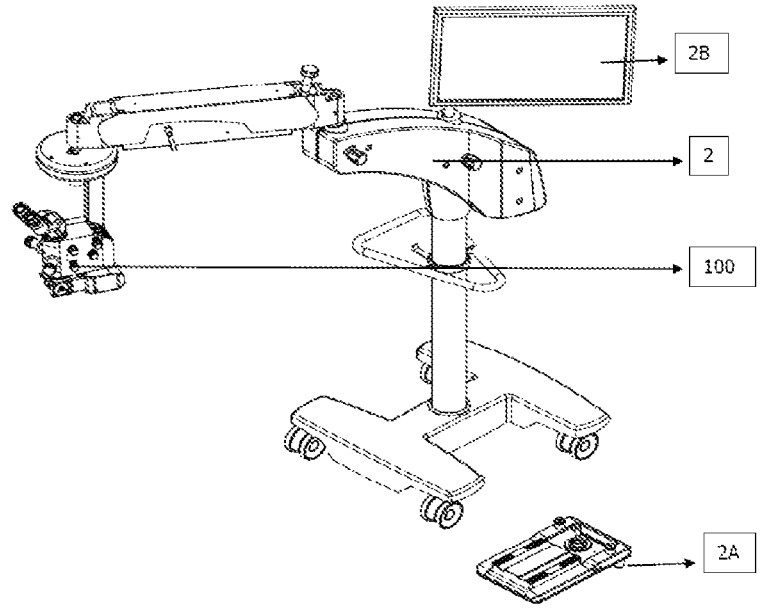
FIG. 4: illustrates single and/or dual wavelength laser delivery system attached to an existing ophthalmic operating microscope according to the present invention.

Referring to FIG. 4, the single and/or dual wavelength laser delivery system [100] is positioned and fixed to the operating microscope's [2] optical head. Said laser delivery system [100] converges and focuses laser wavelength of 532 nm and/or 577 nm laser beam in-line with 635 nm aiming beam to create a circular pattern in order to accomplish a pre-measured Capsulorhexis with a precise circular cut of the capsule in the human eye. The ophthalmic microscope [2] includes a foot switch [2A] for focus adjustment and magnification changes of the operating microscope. The ophthalmic microscope [2] includes a display unit [2B] to display the live image of Capsulorhexis procedure.

Figure 5:
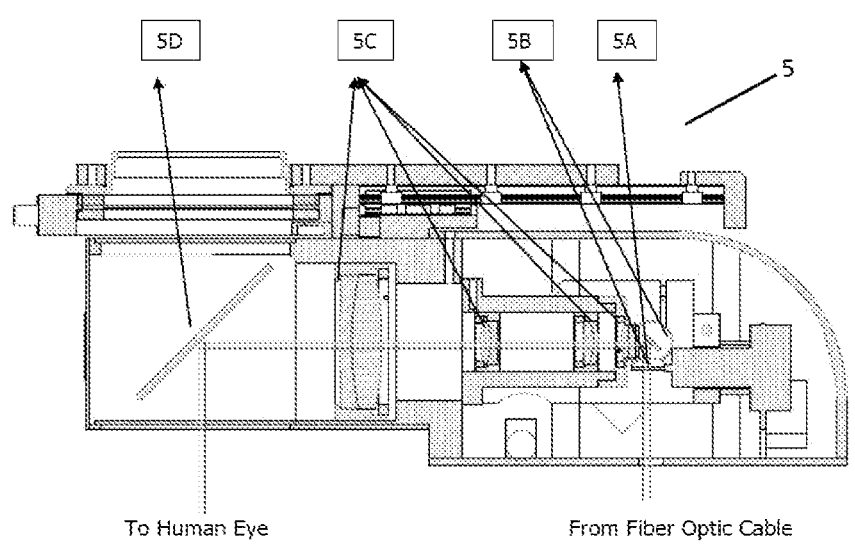
FIG. 5: illustrates delivery system and laser beams according to the present invention.

Referring to FIG. 5, the delivery system [5] comprises of a right-angle prism [5A] and an X and Y Galvo assembly [5B] to generate required laser deflection and a circular laser pattern. The laser beam from the fiber optic cable [6] passes through a focusing lens assembly [5C] to get a required spot size of 100 microns to 300 microns. The laser beam is focused on the human eye using a folding mirror [5D]. The focusing lens assembly [5C] includes four focusing lenses. The folding mirror [5D] is at along the laser optical axis that deflects the laser beam 90 degrees into the human eye capsule to perform the Capsulorhexis. In an aspect, the folding mirror [5D] is mounted on an optics assembly in an angle of 45 degree with a tolerance level of + or −2 degrees.

Figure 6:
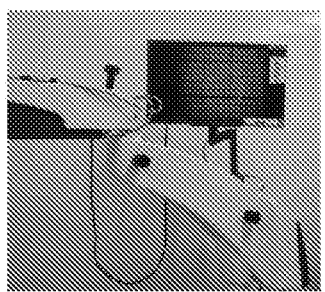
FIG. 6: illustrates the aiming beam RED laser spot and circular diameter of 5.5 mm.
Figure 6:
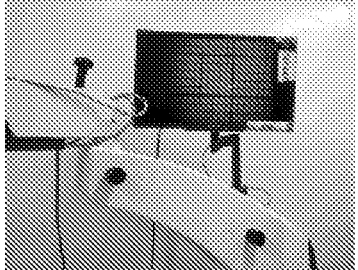

The delivery system [5] converges and focuses laser wavelength of 532 nm and/or 577 nm laser beam to create a circular pattern in order to accomplish a pre-measured Capsulorhexis with a precise circular cut of the capsule in the human eye from diameter 3 mm to 6 mm in steps of 0.5 mm. FIG. 6 shows the aiming beam RED laser spot and circular diameter of 5.5 mm.

Figure 7:
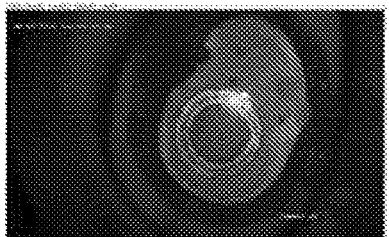
FIG. 7: illustrates the proof of conformity in lab trials of Capsulorhexis in animal eye samples for 5.5 mm and 6 mm diameter.
Figure 7:
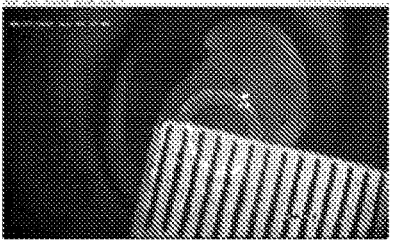
Figure 7:
Figure 7:
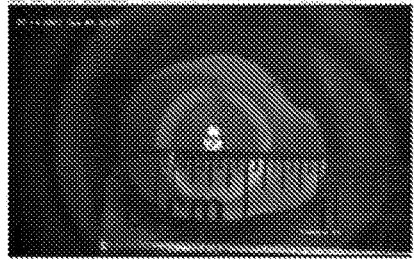

A number of trials of capsulorhexis in animal eyes have been conducted using the single and/or dual (532 and/or 577) nm laser delivery system and have achieved the capsulorhexis in the diameter of 5.5 mm and 6 mm. FIG. 7 illustrates the proof of conformity in lab trials of Capsulorhexis in animal eye samples for 5.5 mm and 6 mm diameter.

Figure 8:
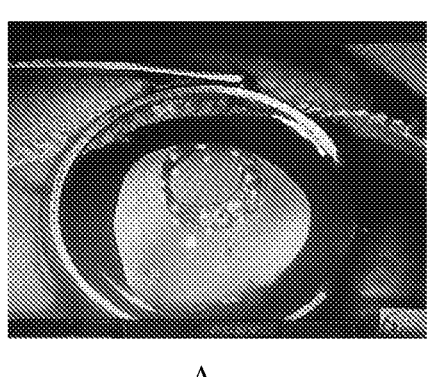
FIG. 8: illustrates the proof of Capsulorhexis trials conducted on animal eyes.
Figure 8:
Figure 8:
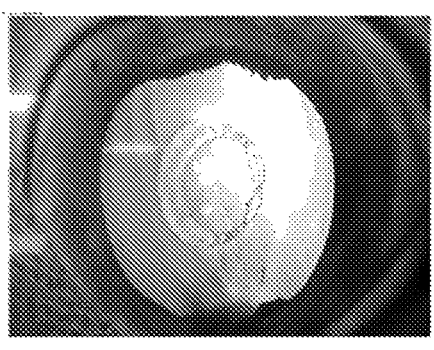
Figure 8:
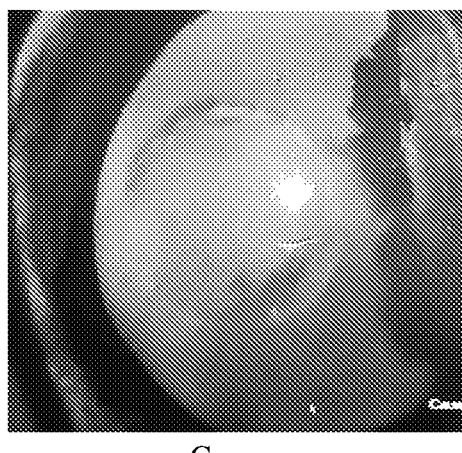
Figure 8:
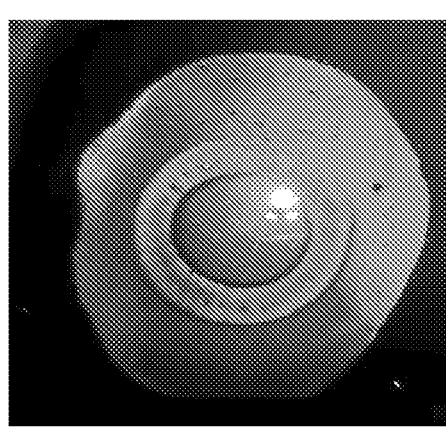

Animal eye lab trials were being conducted from 2020, and have completed 17 trials so far. This process was evolved using different laser powers, laser ON time duration. Standard ophthalmic viscoelastic solution was used to protect the Corneal endothelium cells during the laser ablation procedure and for better capsule identification ophthalmic blue dye solution is used for staining the capsule. Also different concentration of the Ophthalmic blue dye solution was used to observe the absorption level of the two different laser wavelengths (532/577) nm on the capsule tissue under study. FIG. 8A shows the first trial; 8B shows the 10th trial; 8C shows the 12th trial and 8D shows the 15th trial.

The single and/or dual wavelength laser delivery system [100] could be retrofitted to an existing ophthalmic microscope; said system is mounted along the optical axis to suit the requirement, so that it does not obscure the Surgeon's view while operating. The single and/or dual wavelength laser delivery system [100] which could be retrofitted to an existing ophthalmic microscope saves Surgeon time since Patient is not required to be shifted from one Surgical equipment to the other Surgical equipment after the Capsulorhexis is completed, produce accuracy and repeatability in creation of a precise diameter of the capsulorhexis from diameter 3 mm to 6 mm in steps of 0.5 mm. Advantageously, the single and/or dual wavelength laser delivery system

[100] along with the aiming beam provides flexibility and compatibility to the ophthalmic Surgeons.

Working:

For cataract surgery in a human eye, the crystalline lens is replaced with an Intraocular Lens (IOL). The crystalline lens is enclosed in a capsule on front and back side. In conventional cataract surgery, the front portion (anterior) of capsule is circularly removed by 26g needle or capsular forceps and IOL is placed. The present invention is to a system [100] which performs laser assisted procedure to speed up the Cataract surgery of removing the anterior of capsule from diameter 3 mm to 6 mm. In an aspect, anyone of the two wavelengths 532 nm [3] or 577 nm [4] at a given point of time selected by the user is used along with guiding/aiming beam [7] of wavelength 635 nm. The 532 nm or 577 nm is generated in the laser unit [1]. The 532 nm or 577 nm laser along with aiming beam is coupled by focusing lens while leaving the laser unit. The 532 nm or 577 nm laser will enter one end of the fiber optic cable [6] which works in total internal reflection principle without loss and leave the other end. The other end of the fiber optic cable [6] is connected to the delivery system [5] which is mounted in the operating microscope [2]. These lasers leaving the other end of the fiber optic cable [6] passes through the right angle prism [5A], gets deflected by the X and Y Galvo assembly [5B], enters the focusing lens assembly [5C]. These lasers after passing through the focusing lens assembly [5C] is reflected/folded by the folding mirror [5D] and focused on the human eye capsule. By choosing the required laser 532 nm and/or 577 nm and diameter and proper focusing of the microscope, the Capsulorhexis is performed using the foot switch [1A].

We claim:

1. An assembly of a single and/or dual wavelength laser delivery system [100] attached to a microscope, wherein said assembly comprises:

a single and/or dual wavelength laser unit [1];

a delivery system [5]; and an ophthalmic operating microscope [2], wherein the ophthalmic operating microscope [2] is the microscope attached to the single and/or dual wavelength laser delivery system [100], and the ophthalmic operating microscope [2] comprises a binocular unit;

wherein the single and/or dual wavelength laser unit [1] comprises:

an aiming laser beam module configured for emitting an aiming laser beam having a wavelength of 635 nm;

a green laser module [3] combined with the aiming laser beam module, wherein the green laser module [3] and the aiming laser beam module configured for emitting a laser beam having a wavelength of 532 nm from the green laser module [3] along with the aiming laser beam having the wavelength of 635 nm from the aiming laser beam module; and a yellow laser module [4] combined with the aiming laser beam module, wherein the yellow laser module [4] and the aiming laser beam module are configured for emitting a laser beam having a wavelength of 577 nm from the yellow laser module [4] along with the aiming laser beam having the wavelength of 635 nm from the aiming laser beam module;

wherein: (i) the green laser module [3] combined with the aiming laser beam module, or (ii) the yellow laser module [4] combined with the aiming laser beam module, is activated individually for creating a circular pattern with a precise circular cut of a human eye anterior capsule by:

emitting the laser beam having the wavelength of 532 nm from the green laser module [3] along with the aiming laser beam having the wavelength of 635 nm from the aiming laser beam module, such that the aiming laser beam having the wavelength of 635 nm is used to locate and guide a user of said assembly to aim the laser beam having the wavelength of 532 nm, or emitting the laser beam having a wavelength of 577 nm from the yellow laser module [4] along with the aiming laser beam having the wavelength of 635 nm from the aiming laser beam module, such that the aiming laser beam having the wavelength of 635 nm is used to locate and guide the user of said assembly to aim the laser beam having the wavelength of 577 nm;

wherein each of the laser modules [3 and 4] comprises a low pass filter [3A and 4A] and a focusing lens [3B and 4B] respectively, wherein the green laser module [3] and the yellow laser module [4] are connected to the delivery system [5] through a single fiber optic cable [6], wherein the single fiber optic cable [6] is interchanged between the green laser module [3] and the yellow laser module [4], as required by the user of said assembly;

wherein the delivery system [5] comprises a right-angle prism [5A]; a X and Y Galvo assembly [5B]; a focusing lens assembly [5C]; and a folding mirror [5D], wherein the single and/or dual wavelength laser unit [1] emits said laser beams that pass through the fiber optic cable [6], such that said laser beams get reflected using the right angle prism [5A], get deflected by the X and Y Galvo assembly [5B], enter the focusing lens assembly [5C], get reflected by a folding mirror [5D], and get focused on the human eye anterior capsule perpendicularly at 90 degrees with reference to a horizontal plane of an eye ball, wherein the folding mirror bends reflected said laser beams and emitted said laser beams to focus on the human eye anterior capsule perpendicularly at 90 degrees with reference to the horizontal plane of the eye ball, wherein said laser delivery system [100] attached to the binocular unit of the microscope converges and focuses the laser beam having the wavelength of 532 nm and the laser beam having the wavelength of 577 nm in-line with the aiming laser beam having the wavelength of 635 nm to create a circular pattern to accomplish a pre-measured Capsulorhexis with a precise circular cut of the human eye anterior capsule.

2. The assembly of claim 1, wherein the low pass filters [3A and 4A] are mounted at an angle that transmits the laser beam having the wavelength of 532 nm or the laser beam having the wavelength of 577 nm and reflects the aiming laser beam having the wavelength of 635 nm.

3. The assembly of claim 1, wherein said laser beams from the fiber optic cable [6] pass through the focusing lens assembly [5C] to get a required spot size of 100 microns to 300 microns.

4. The assembly of claim 1, wherein the folding mirror [5D] is mounted in an angle of 45 degrees with a tolerance level of + or −2 degrees along the laser optical axis.

5. The assembly of claim 1, wherein the single and/or dual wavelength laser delivery system [100] has a pre-setting, such that the single and/or dual wavelength laser delivery system [100] converges and focuses the laser beam having the wavelength of 532 nm and the laser beam having the wavelength of 577 nm in-line with the aiming laser beam having the wavelength of 635 nm to create a circular pattern to accomplish a pre-measured Capsulorhexis with a precise circular cut of the human eye anterior capsule with a precise diameter of 3 mm to 6 mm in steps of 0.5 mm, due to the pre-setting.

6. The assembly of claim 1, wherein the laser unit [1] comprises a foot switch [1A] to trigger the laser beam having the wavelength of 532 nm and/or the laser beam having the wavelength of 577 nm.

\* \* \* \* \*